(12) United States Patent
Osawa

(10) Patent No.: US 8,961,422 B2
(45) Date of Patent: Feb. 24, 2015

(54) ULTRASONIC PROBE

(75) Inventor: Atsushi Osawa, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 1543 days.

(21) Appl. No.: 12/035,179

(22) Filed: Feb. 21, 2008

(65) Prior Publication Data

US 2008/0200812 A1      Aug. 21, 2008

(30) Foreign Application Priority Data

Feb. 21, 2007 (JP) ................................. 2007-040133

(51) Int. Cl.
| | |
|---|---|
| A61B 8/14 | (2006.01) |
| A61B 8/00 | (2006.01) |
| A61B 8/12 | (2006.01) |
| A61B 8/08 | (2006.01) |
| B06B 1/06 | (2006.01) |
| G01S 15/89 | (2006.01) |

(52) U.S. Cl.
CPC ............. A61B 8/4488 (2013.01); A61B 8/12 (2013.01); A61B 8/483 (2013.01); B06B 1/0633 (2013.01); G01S 15/8909 (2013.01); A61B 8/445 (2013.01)
USPC .............. 600/459; 600/447; 29/594; 310/334

(58) Field of Classification Search
CPC ... B06B 1/0622; H01L 41/083; H01L 41/293; A61B 8/4483
See application file for complete search history.

(56) References Cited

U.S. PATENT DOCUMENTS

| | | | | | |
|---|---|---|---|---|---|
| 3,833,825 | A | * | 9/1974 | Haan .............................. | 310/320 |
| 5,415,175 | A | * | 5/1995 | Hanafy et al. ................. | 600/459 |
| 5,438,998 | A | * | 8/1995 | Hanafy .......................... | 600/459 |
| 5,465,724 | A | * | 11/1995 | Sliwa et al. .................... | 600/459 |
| 6,014,473 | A | * | 1/2000 | Hossack et al. ............... | 382/294 |
| 6,043,589 | A | * | 3/2000 | Hanafy .......................... | 310/335 |
| 6,368,276 | B1 | * | 4/2002 | Bullis ............................ | 600/437 |
| 6,415,485 | B1 | * | 7/2002 | Hanafy .......................... | 29/25.35 |
| 6,511,427 | B1 | * | 1/2003 | Sliwa et al. .................... | 600/438 |
| 6,537,220 | B1 | * | 3/2003 | Friemel et al. ................. | 600/447 |
| 6,566,265 | B2 | * | 5/2003 | Esashi et al. .................. | 438/689 |
| 6,656,124 | B2 | * | 12/2003 | Flesch et al. .................. | 600/459 |
| 6,691,387 | B2 | * | 2/2004 | Hanafy ......................... | 29/25.35 |

(Continued)

FOREIGN PATENT DOCUMENTS

| JP | 04152938 A | 5/1992 |
|---|---|---|
| JP | 2000-214144 A | 8/2000 |

(Continued)

OTHER PUBLICATIONS

Japanese Office Action corresponding to Japanese Patent Application No. 2007-040133, dated Aug. 30, 2011.

*Primary Examiner* — Nicholas Evoy
(74) *Attorney, Agent, or Firm* — Sughrue Mion, PLLC

(57) ABSTRACT

An ultrasonic probe that can be relatively easily manufactured and has a desired ultrasonic radiation surface. The ultrasonic probe includes: plural supporting materials, each having a principal surface on which plural signal wires are formed, the plural supporting materials arranged such that the principal surfaces are oriented in different directions from one another; plural groups of ultrasonic transducers, plural ultrasonic transducers in each group having plural electrodes formed on side surfaces, the plural electrodes respectively joined to the plural signal wires formed on the principal surface of the respective one of the plural supporting materials.

9 Claims, 17 Drawing Sheets

(56) References Cited

U.S. PATENT DOCUMENTS

| | | | |
|---|---|---|---|
| 6,752,763 B2* | 6/2004 | Erikson | 600/459 |
| 6,776,762 B2* | 8/2004 | Erikson et al. | 600/459 |
| 6,875,178 B2* | 4/2005 | Phelps et al. | 600/447 |
| 6,891,311 B2* | 5/2005 | Phelps et al. | 310/317 |
| 6,994,674 B2* | 2/2006 | Sheljaskow et al. | 600/459 |
| 7,268,017 B2* | 9/2007 | Osawa | 438/113 |
| 7,367,947 B2* | 5/2008 | Brock-Fisher | 600/447 |
| 7,795,786 B2* | 9/2010 | Nakayama et al. | 310/334 |
| 7,797,804 B2* | 9/2010 | Nakamura et al. | 29/25.35 |
| 8,323,201 B2* | 12/2012 | Towfiq et al. | 600/459 |
| 2002/0108220 A1 | 8/2002 | Hanafy | 29/25.35 |
| 2002/0156373 A1* | 10/2002 | Wakabayashi et al. | 600/437 |
| 2003/0009153 A1* | 1/2003 | Brisken et al. | 604/890.1 |
| 2003/0011285 A1* | 1/2003 | Ossmann | 310/334 |
| 2003/0073906 A1* | 4/2003 | Flesch et al. | 600/459 |
| 2003/0163046 A1* | 8/2003 | Nohara et al. | 600/443 |
| 2004/0002656 A1* | 1/2004 | Sheljaskow et al. | 600/459 |
| 2005/0113689 A1* | 5/2005 | Gritzky | 600/437 |
| 2005/0119576 A1* | 6/2005 | Li | 600/459 |
| 2005/0203409 A1* | 9/2005 | Frey et al. | 600/459 |
| 2005/0288588 A1* | 12/2005 | Weber et al. | 600/447 |
| 2006/0052699 A1* | 3/2006 | Angelsen et al. | 600/437 |
| 2006/0052707 A1* | 3/2006 | Dickinson et al. | 600/466 |
| 2006/0076650 A1* | 4/2006 | Osawa | 257/620 |
| 2006/0173348 A1* | 8/2006 | Wilser et al. | 600/466 |
| 2006/0241452 A1* | 10/2006 | Cerofolini | 600/444 |
| 2007/0078340 A1* | 4/2007 | Wilcox et al. | 600/437 |
| 2007/0167815 A1* | 7/2007 | Jacobsen et al. | 600/459 |
| 2007/0182288 A1* | 8/2007 | Nakamura et al. | 310/340 |
| 2008/0045838 A1* | 2/2008 | Hyuga | 600/463 |
| 2008/0125659 A1* | 5/2008 | Wilser et al. | 600/459 |
| 2008/0238259 A1* | 10/2008 | Osawa | 310/334 |
| 2009/0119896 A1* | 5/2009 | Nakamura et al. | 29/25.35 |
| 2009/0236940 A1* | 9/2009 | Nakayama et al. | 310/336 |
| 2009/0243442 A1* | 10/2009 | Osawa | 310/366 |

FOREIGN PATENT DOCUMENTS

| | | |
|---|---|---|
| JP | 2001-292496 A | 10/2001 |
| JP | 2001-309493 A | 11/2001 |
| JP | 2005-210245 A | 8/2005 |
| WO | 0121072 A1 | 3/2001 |

* cited by examiner

ULTRASONIC PROBE

BACKGROUND OF THE INVENTION

1. Field of the Invention

The present invention relates to an ultrasonic probe to be used when extracavitary scan or intracavitary scan is performed on an object to be inspected.

2. Description of a Related Art

In medical fields, various imaging technologies have been developed in order to observe the interior of an object to be inspected and to make diagnoses. Especially, ultrasonic imaging for acquiring interior information of the object by transmitting and receiving ultrasonic waves enables image observation in real time, and provides no exposure to radiation unlike other medical image technologies such as X-ray photography or RI (radio isotope) scintillation camera. Accordingly, ultrasonic imaging is utilized as an imaging technology at a high level of safety in a wide range of departments including not only the fetal diagnosis in the obstetrics, but gynecology, circulatory system, digestive system, etc.

The ultrasonic imaging is an image generation technology utilizing the nature of ultrasonic waves that the waves are reflected at a boundary between regions with different acoustic impedances (e.g., a boundary between structures). Typically, an ultrasonic imaging apparatus (or referred to as an ultrasonic diagnostic apparatus or an ultrasonic observation apparatus) is provided with an ultrasonic probe to be used in contact with the object or ultrasonic probe to be used by being inserted into a body cavity of the object. Alternatively, the ultrasonic imaging apparatus may be provided with an ultrasonic endoscope in combination of an endoscope for optically observing the interior of the object and an ultrasonic probe for intracavity. From such an ultrasonic probe or ultrasonic endoscope (hereinafter, refereed to as an ultrasonic probe or the like), ultrasonic beams are transmitted toward the object such as a human body and ultrasonic echoes generated in the object are received by using the ultrasonic probe or the like, and thereby, ultrasonic image information is acquired. On the basis of the ultrasonic image information, contours of structures (e.g., internal organs, diseased tissues, or the like) existing within the object are extracted by obtaining reflection points, where ultrasonic echoes have been generated, and reflection intensity.

In a general ultrasonic probe, an ultrasonic transducer for transmitting and receiving ultrasonic waves is configured of a vibrator (piezoelectric vibrator) having electrodes formed on both sides of a material that has a piezoelectric property (a piezoelectric material) such as a piezoelectric ceramics represented by PZT (Pb (lead) zirconate titanate), a polymeric piezoelectric material represented by PVDF (polyvinylidene difluoride), or the like. When a pulsed or continuous wave voltage is applied to the electrodes of the vibrator, the piezoelectric material expands and contracts. By the expansion and contraction, pulsed or continuous wave ultrasonic waves are generated from the respective vibrators, and an ultrasonic beam is formed by synthesizing these ultrasonic waves. Further, the respective vibrators expand and contract by receiving propagating ultrasonic waves to generate electric signals. These electric signals are outputted as detection signals of the ultrasonic waves. A plurality of such ultrasonic transducers are arranged and sequentially driven, and thereby, an ultrasonic beam is formed by synthesizing ultrasonic waves transmitted from the respective ultrasonic transducers for electric scan of the object.

There are various kinds of ultrasonic probes such as a one-dimensional-array probe, a two-dimensional-array probe, an annular-array probe, and so on according to arrangement of plural ultrasonic transducers, and ultrasonic probes of linear-scan type, sector-scan type, convex-scan type, radial-scan type, and so on according to scan type.

Among them, a two-dimensional array probe in which plural ultrasonic transducers are two-dimensionally arranged especially attracts attention. This is because, using the two-dimensional array probe, two-dimensional scan of the object is possible with an ultrasonic beam without moving the probe itself, and three-dimensional ultrasonic image information including information in the depth direction of the object (the traveling direction of ultrasonic waves) can be obtained. Thereby, an image representing a desired section of the object can be constructed and a stereoscopic image (3D image) of the object can be constructed (volume imaging can be performed).

If it is possible to generate a three-dimensional image by ultrasonic imaging, very useful diagnoses can be made in various medical fields. For example, in the obstetrics department, fetal diagnoses by observation of developing and growing of a fetus in real time in moving pictures can be performed. Specifically, early detection and treatment of fetal abnormality or the like may be possible by continuous observation of the volume change of a brain and growth of a spine. Alternatively, an attempt to provide treatment of a fetus within a body cavity is being made while referring to three-dimensional ultrasonic images. Further, in the cardiovascular department, a heart disease can be discovered by observation of volume change of a heart or the like based on three-dimensional ultrasonic images. Such demand is especially high in Europe and the United States. Furthermore, in the urologic field, there is so much interest in three-dimensional ultrasonic images.

However, there are much harder technical problems in fabrication of two-dimensional arrays than those for one-dimensional arrays. First, when ultrasonic transducers are arranged in a two-dimensional manner, the number of ultrasonic transducers dramatically increases. Accordingly, electrically leading out wires from the respective ultrasonic transducers becomes difficult. Secondly, since the number of shield wires drastically increases with the number of ultrasonic transducers, a cable for connecting the ultrasonic probe and an ultrasonic diagnostic apparatus main body becomes thick. Thereby, handling of the ultrasonic probe becomes difficult. Further, the large cable diameter is a critical defect in the ultrasonic probe for intracavitary observation.

As a related technology, Japanese Patent Application Publication JP-P2001-292496A discloses an electrode lead-out structure of a two-dimensional array probe. That is, in JP-P2001-292496A, the two-dimensional array probe is formed by connecting to one another a two-dimensional transducer, in which signal wires are passed through a backing material and signal electrodes as one ends of the signal wires are two-dimensionally arranged as an electrode pattern in parallel with the arrangement surface of vibrating elements, a relay substrate, on which the same electrode pattern as that of the signal electrodes, and an IC substrate to be coupled perpendicularly to the relay substrate.

However, according to the method of leading out wires, the connection of address electrodes may be uncertain. Therefore, it is extremely difficult to ensure the connection between 1000 to 4000 ultrasonic transducers, for example, and the electric wires, respectively.

Japanese Patent Application Publication JP-P2000-214144A discloses that, in an ultrasonic probe having vibrators arranged in a two-dimensional matrix form, an electric circuit connected to the respective vibrator elements for transmitting and receiving signals is configured of signal wires one-dimensionally arranged on a base film at intervals corresponding to that of the vibrator elements, and the two-dimensional arrangement ultrasonic probe is formed by sandwiching the base film part of the connection probe to the vibrator elements of the signal wires between acoustic absorbing materials to bond them. That is, in JP-P2000-214144A, the base films (flexible pattern circuits), on which plural signal wires are respectively formed, and the acoustic absorbing materials (backing materials) are alternately joined, and thereby, ends of the plural signal wires are two-dimensionally arranged in alignment with the arrangement of the vibrators in the two-dimensional matrix form.

However, in JP-P2000-214144A, connection uncertainty between the respective vibrators and the signal wires also remains. Further, according to the fabrication method of the ultrasonic probe disclosed in JP-P2000-214144A, since the ultrasonic transducers are arranged to form an ultrasonic radiation surface as a flat surface, it is possible to fabricate a flat array (sector scan array) to be used for chest observation, for example. However, it is impossible to fabricate a convex array having an ultrasonic radiation surface entirely with a convex surface (e.g., to be used for fetus observation).

Japanese Patent Application Publication JP-P2001-309493A discloses a two-dimensional array ultrasonic probe having a structure in which print substrates for leading out signal leads and ground wires from the respective vibrators at the respective column intervals of elements arranged in a matrix form is provided, and that a two-dimensional array transducer is formed by mounting a vibrator array for one column on the print substrate and then arranging the print substrates, on which the vibrators have been mounted, in the row direction.

Further, Japanese Patent Application Publication JP-P2005-210245A discloses that units, each including a print substrate, plural wiring lines formed with a predetermined pitch on the print substrate, plural multilayered piezoelectric elements arranged in one row such that the first sides of the elements contact with ends of the wiring lines respectively, a conducting thin plate that commonly connects the second sides opposite to the first sides of the plural multilayered piezoelectric elements arranged in one row, and a backing material formed to cover the wiring lines on the print substrate, are formed by being arranged side by side with a predetermined pitch. Further, the first sides and the second sides of the multilayered piezoelectric elements have conductivity, and, in the multilayered piezoelectric elements, plural piezoelectric materials and plural internal electrode layers are alternately stacked and the plural internal electrode layers are alternately connected to ones of the first sides or the second sides.

In JP-P2001-309493A and JP-P2005-210245A, a unit is fabricated by forming plural wiring lines side by side on a flexible print substrate, and connecting plural ultrasonic transducers to the wiring lines on side surfaces (surfaces perpendicular to the ultrasonic radiation surface) respectively. Then, a two-dimensional array is fabricated by stacking a plurality of the units. According to the fabrication method, the signal wire of each ultrasonic transducer can be reliably connected. However, it is also impossible to form the ultrasonic radiation surface of the two-dimensional array as a curved surface.

SUMMARY OF THE INVENTION

Accordingly, the present invention has been achieved in view of the above-mentioned problems. A purpose of the present invention is to provide an ultrasonic probe that can be relatively easily manufactured and has a desired ultrasonic radiation surface.

In order to accomplish the above-mentioned purpose, an ultrasonic probe according to one aspect of the present invention includes: plural supporting materials, each having a principal surface on which plural signal wires are formed, the plural supporting materials arranged such that the principal surfaces are oriented in different directions from one another; plural groups of ultrasonic transducers, plural ultrasonic transducers in each group having plural electrodes formed on side surfaces, the plural electrodes respectively joined to the plural signal wires formed on the principal surface of the respective one of the plural supporting materials.

According to the present invention, an ultrasonic probe having a desired ultrasonic radiation surface can be relatively easily manufactured by arranging supporting materials, on which plural ultrasonic transducers are joined, to be oriented in different directions from one another.

DESCRIPTION OF THE PREFERRED EMBODIMENTS

Hereinafter, embodiments of the present invention will be explained in detail with reference to the drawings. The same reference numbers will be assigned to the same component elements and the description thereof will be omitted.

Figure 1:
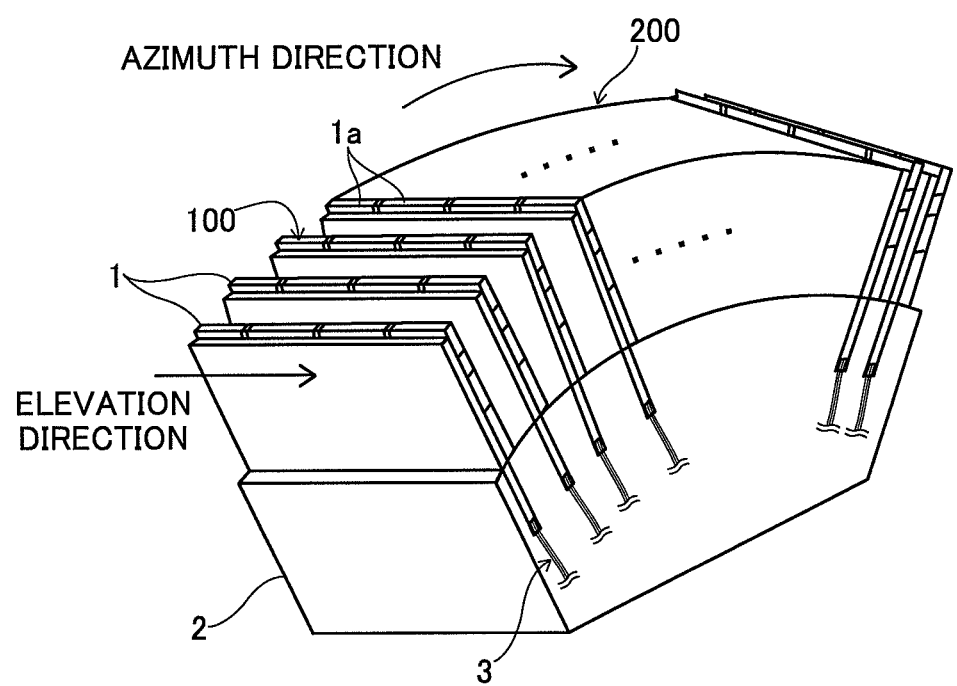
FIG. 1 is a perspective view showing a structure of an ultrasonic probe according to the first embodiment of the present invention.

FIG. 1 is a perspective view showing an exterior appearance of an ultrasonic probe according to the first embodiment of the present invention. As shown in FIG. 1, the ultrasonic probe according to the embodiment includes plural one-dimensional arrays 1. Each one-dimensional array 1 includes plural (four in FIG. 1) ultrasonic transducers 1a one-dimensionally arranged in the elevation direction. Such one-dimensional arrays 1 are radially arranged in the azimuth direction (scan direction). Thereby, a two-dimensional ultrasonic radiation surface 200 formed by ultrasonic radiation surfaces 100 of the plural ultrasonic transducers 1a becomes entirely a desired shape (a curved surface corresponding to part of the side surface of a cylinder in FIG. 1).

These one-dimensional arrays 1 are held by a backing material (that also serves as a holding member) 2 formed from a material having great acoustic attenuation. As the material of the backing material 2, for example, a material formed by mixing and dispersing powder of ferrite, metal, PZT, tungsten carbide or the like in a resin material such as epoxy or natural rubber is used. In FIG. 1, a column having a convex upper surface is shown as the backing material 2, however, the shape of the backing material 2 is not limited to the shape shown in FIG. 1, but may be a semi-column or sector column.

Further, lead wires 3 are connected to the one-dimensional arrays 1, respectively.

Figure 2:
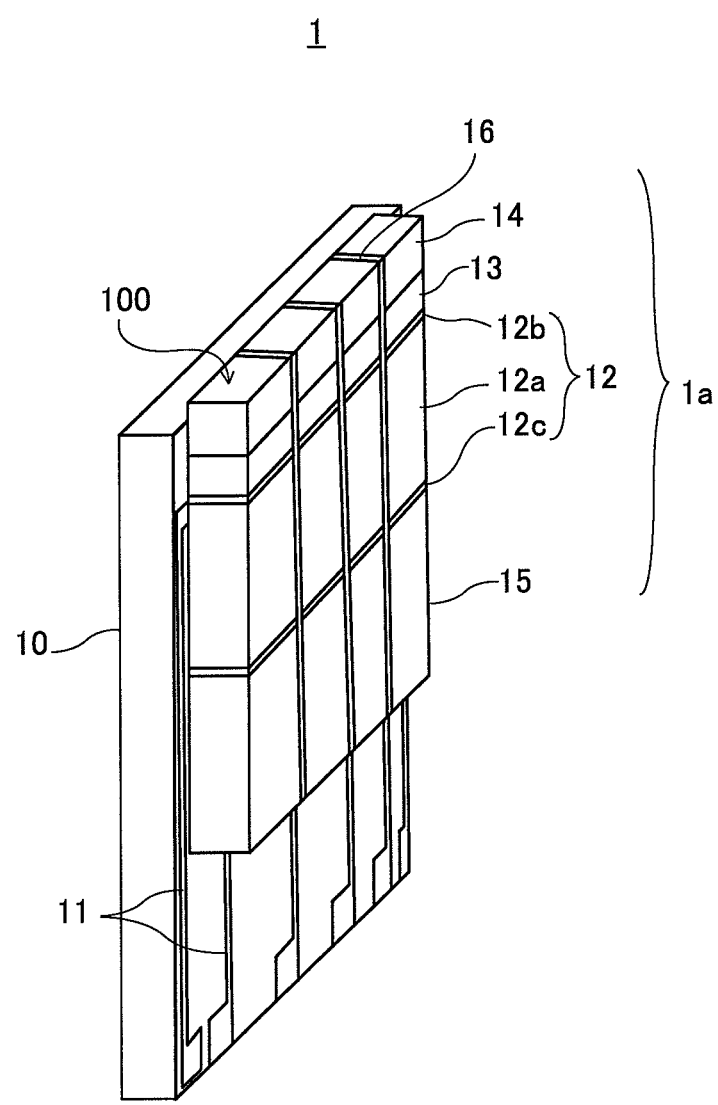
FIG. 2 is a perspective view showing a structure of a one-dimensional array shown in FIG. 1.

FIG. 2 is a perspective view showing a structure of the one-dimensional array 1 shown in FIG. 1. Each one-dimensional array 1 includes a substrate 10 on which wires 11 have been formed, and plural ultrasonic transducers 1a joined to the substrate 10 at the side surfaces (the surfaces different from the ultrasonic radiation surface 100 and the opposite side surface). The substrate 10 is used as a supporting material for supporting the plural ultrasonic transducers 1a.

Each ultrasonic transducer 1a includes at least a vibrator (piezoelectric vibrator) for transmitting and receiving ultrasonic waves and an acoustic matching layer 13, and may further include an acoustic lens 14 and a backing layer 15. Further, filling materials 16 may be provided between the adjacent two ultrasonic transducers 1a.

The substrate 10 is formed from a hard material such as silicon (Si), silicon oxide ($SiO_2$), silicon carbide (SiC), glass epoxy, polyimide, alumina ($Al_2O_3$) and zirconia, and has a thickness of about 50 μm to 100 μm, for example. As the hardness of the substrate 10, it is sufficient to have rigidity to the degree that, when a part of the substrate 10 is inserted into the backing material 2, the part protruding from the backing material 2 (FIG. 1) may not be unstable, desirably, may stand upright. Further, in the case where a silicon chip is used as the substrate 10, the wires 11 may be formed by a semiconductor process. In this case, narrow pitch wires can be formed in a short process.

The wires 11 are transmission paths for supplying drive signals to the vibrators 12, which will be described later, and transmitting electric signals outputted from the vibrators 12. The lead wires 3 shown in FIG. 1 are connected to those wires 11.

The vibrator 12 includes a piezoelectric material 12a such as a piezoelectric ceramics represented by PZT (Pb (lead) zirconate titanate), a polymeric piezoelectric material represented by PVDF (polyvinylidene difluoride), or the like, and electrodes 12b and 12c formed on both sides thereof. When a pulsed or continuous wave voltage is applied to these electrodes, the piezoelectric material expands and contracts, and, by the expansion and contraction, pulsed or continuous wave ultrasonic waves are generated from the respective vibrators.

The acoustic matching layer 13 is formed from Pyrex (registered trademark) glass or an epoxy resin containing metal powder, which easily propagates ultrasonic waves, for example, and provided at the ultrasonic radiation surface 100 side so as to eliminate mismatch of acoustic impedances between the object as a living body and the ultrasonic transducers 12. Thereby, the ultrasonic waves transmitted from the ultrasonic transducers efficiently propagate within the object. Although the single-layer of acoustic matching layer 13 has been shown in FIG. 2, plural acoustic matching layers may be provided according to need.

The acoustic lens 14 is formed from silicone rubber, for example, and focuses an ultrasonic beam transmitted from the plural ultrasonic transducers 1a and propagating through the acoustic matching layer 13 at a predetermined depth within the object.

The backing layer 15 is formed from a material having great acoustic attenuation such as an epoxy resin containing ferrite powder, metal powder, or PZT powder, or rubber containing ferrite powder, and promotes attenuation of unwanted ultrasonic waves generated from the vibrator 12.

Further, the filling material 16 stabilizes the positions of the respective ultrasonic transducers 1a and reduces interference among the plural vibrators 12.

Such ultrasonic transducers 1a are attached to the substrate 10 by joining the electrodes 12b and 12c of the vibrators 12 to the wires 11 by using electrically conductive paste (not shown). The electrically conductive paste is an adhesive formed by mixing metal powder in a resin base material such as an epoxy resin, for example. By using the electrically conductive paste, the conductivity between the wires 11 and the vibrators 12 is ensured. Further, since the electrically conductive paste has a certain degree of elasticity, braking on the expansion and contraction of the vibrators 12 can be reduced compared to the case of using solder, for example.

Figure 3:
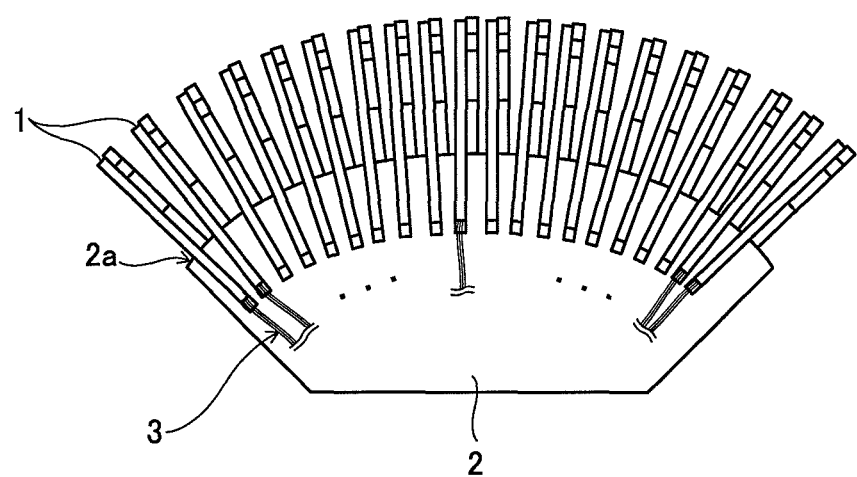
FIG. 3 is a side view showing the ultrasonic probe shown in FIG. 1.

FIG. 3 shows a side surface of the ultrasonic probe shown in FIG. 1. As shown in FIG. 3, plural grooves 2a are formed on the backing material 2, and the one-dimensional arrays 1 are held by inserting the substrates 10 shown in FIG. 2 into the grooves 2a to the lower ends of the backing layers 15. Further, the lead wires 3 connected to the respective one-dimensional arrays 1 are led out to the side of the backing material 2 through the bottom parts of the grooves 2a.

Next, a method of manufacturing the ultrasonic probe according to the first embodiment of the present invention will be explained.

Figure 4:
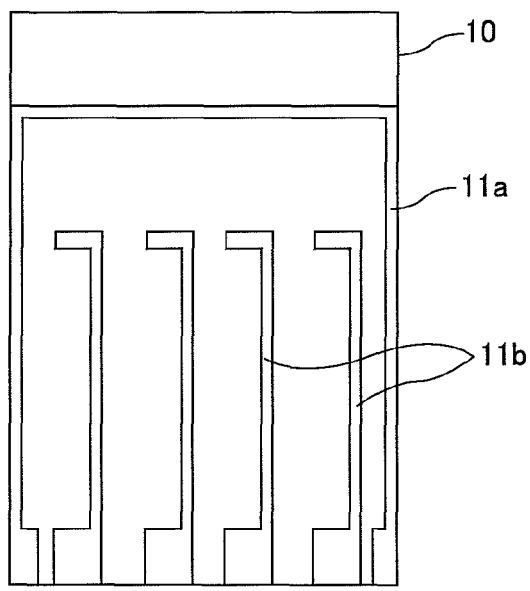
FIG. 4 is a plan view showing a substrate on which wires have been formed.

First, as shown in FIG. 4, a hard material such as silicon (Si) is shaped in a shape of the substrate 10, and a common wire 11a to be connected to the plural vibrators 12 and individual wires 11b corresponding to the respective vibrators 12 (FIG. 2) are formed thereon. As a method of forming wires, a general technique such as a lift off technique may be utilized, or a semiconductor process may be used when a silicon chip is used as the substrate.

Figure 5:
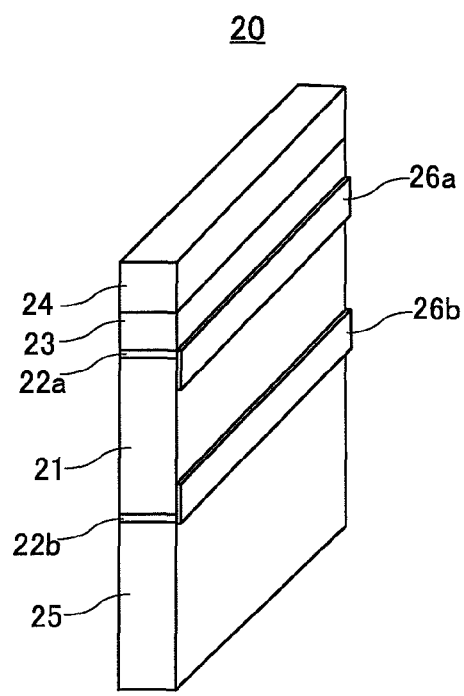
FIG. 5 is a perspective view showing a plate-like ultrasonic transducer member.

On the other hand, as shown in FIG. 5, a plate-like ultrasonic transducer member 20 is fabricated. That is, first, electrode layers 22a and 22b are formed on both sides of a piezoelectric material 21 according to a general method such as evaporation or sputtering. In this regard, the electrode layers 22a and 22b are bent along the side surface of the piezoelectric material 21 (bent electrodes 26a and 26b). Then, an acoustic matching layer 23 and an acoustic lens 24 are provided at one electrode layer 22a side, and a backing layer 25 is provided at the other electrode layer 22b side. These layers (the acoustic matching layer 23, the acoustic lens 24, and the backing layer 25) may be formed by joining the respective shaped members by using an adhesive of synthetic resin, for example.

Figure 6:
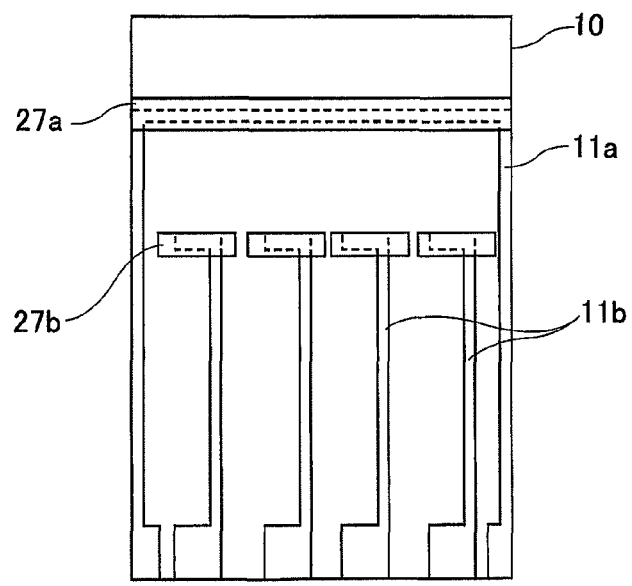
FIGS. 6 and 7 are diagrams for explanation of the step of joining the substrate and the ultrasonic transducer member to each other.
Figure 7:
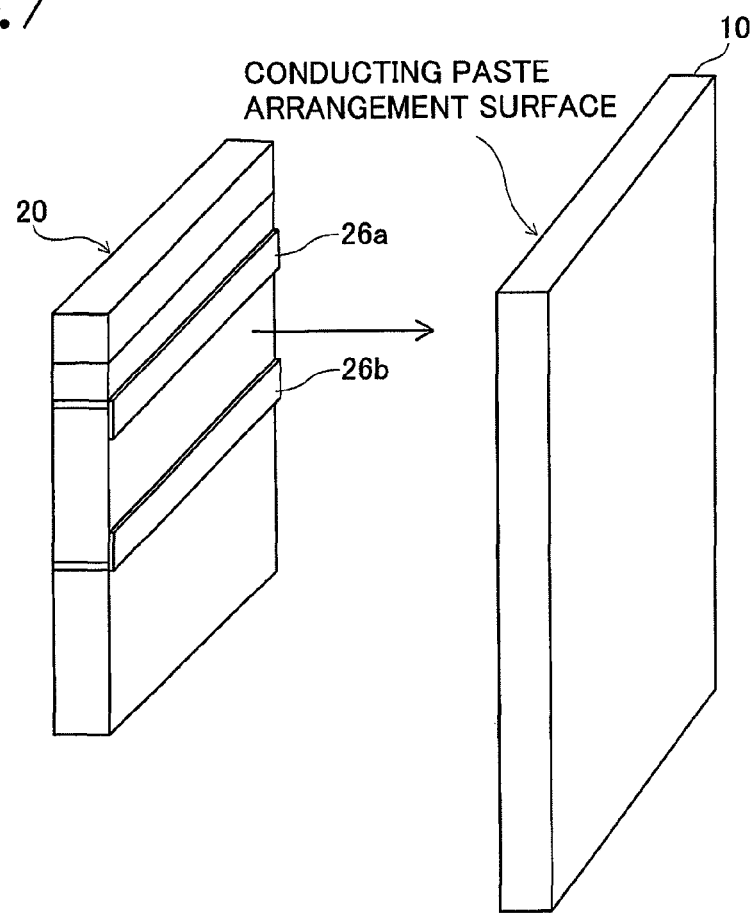
Figure 8:
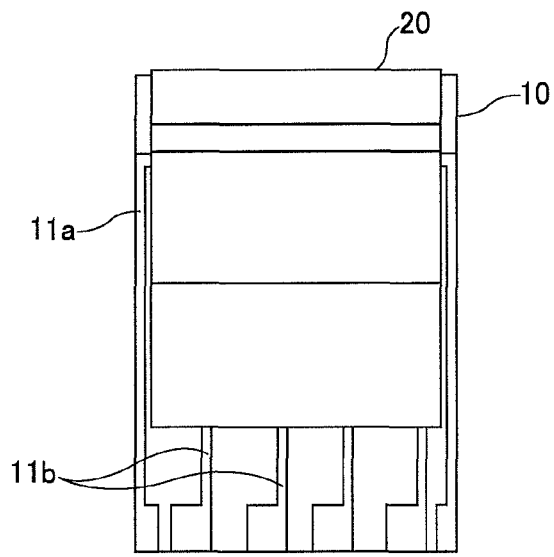
FIG. 8 is a schematic view showing the ultrasonic transducer member joined to the substrate.

Then, as shown in FIG. 6, electrically conductive pastes 27a and 27b are provided on the parts to be joined to the bent electrodes 26a and 26b of the ultrasonic transducer member 20 (FIG. 5) within the common wire 11a and the individual wires 11b formed on the substrate 10. Then, as shown in FIG. 7, the surface on which the electrically conductive pastes of the substrate 10 have been provided and the surface on which the bent electrodes 26a and 26b of the ultrasonic transducer member 20 have been formed are bonded. Thereby, as shown in FIG. 8, the substrate 10 and the ultrasonic transducer member 20 are integrated.

Here, it is desirable that the electrically conductive pastes 27a and 27b are provided to be thicker for less braking on the expansion and contraction of the vibrators 12 (FIG. 2). For example, the thickness of about 10 μm to 20 μm of the electrically conductive pastes 27a and 27b can make the vibrators 12 to vibrate, and the thickness of about 30 μm to 50 μm is sufficient.

Figure 9:
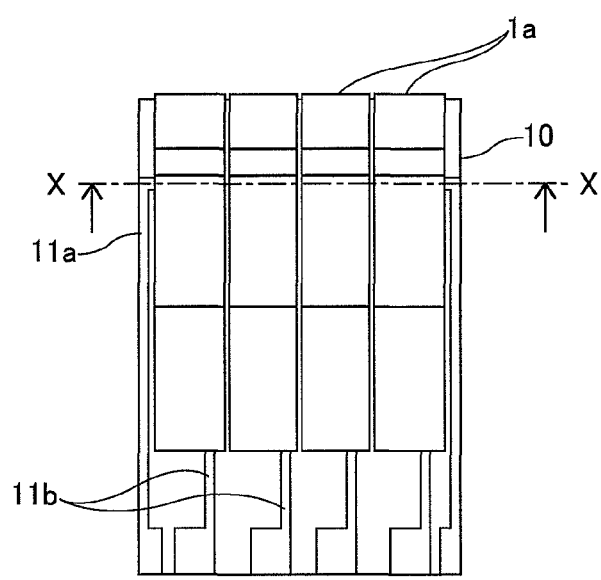
FIG. 9 is a plan view for explanation of the step of dicing the ultrasonic transducer member.
Figure 10:
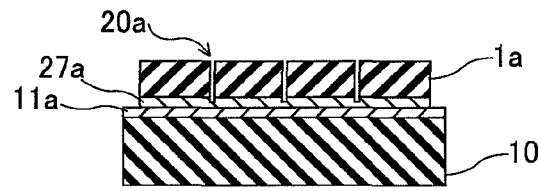
FIG. 10 is a sectional view for explanation of the step of dicing the ultrasonic transducer member.
Figure 11:
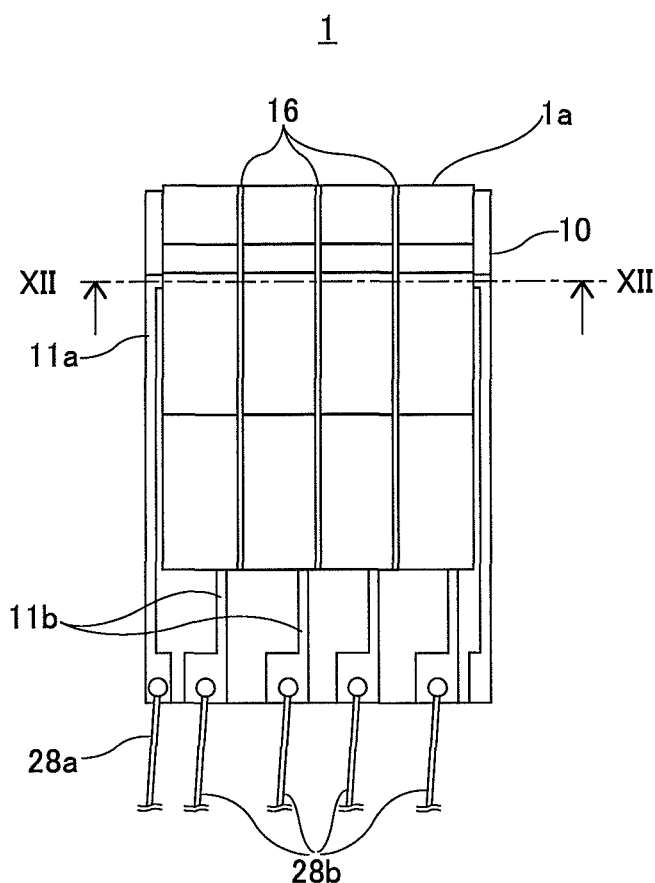
FIG. 11 is a plan view showing the one-dimensional array on which wires have been formed.
Figure 12:
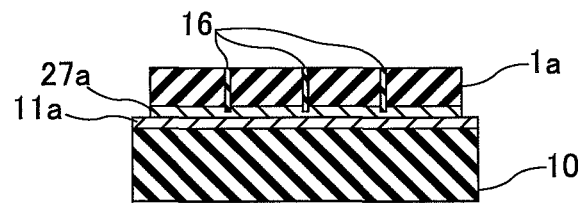
FIG. 12 is a sectional view showing the one-dimensional array on which wires have been formed.

Then, as shown in FIG. 9, the ultrasonic transducer member 20 is diced into plural ultrasonic transducers 1a. In this regard, as shown in FIG. 10, dicing is stopped at the depth close to the wire 11a (preferably, at the middle of the electrically conductive paste 27a) so as not to cut the wires 11a. Then, as shown in FIGS. 11 and 12, synthetic resin filling materials 16 are provided in the grooves 20a formed by dicing. Thereby, the one-dimensional array 1 is completed.

Furthermore, then, as shown in FIG. 11, a ground lead-out wire 28a is connected to the common wire 11a by using solder and address lead-out wires 28b are connected to the individual wires 11b by using solder.

Figure 13:
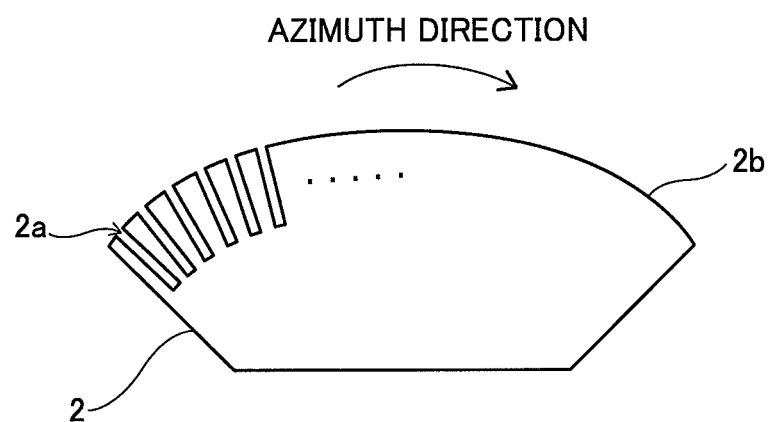
FIG. 13 is a diagram for explanation of the step of preparing a backing material.

Further, the backing material 2 for holding plural one-dimensional arrays 1 is separately fabricated. That is, as shown in FIG. 13, an upper surface 2b of a resin material or the like, in which ferrite powder or the like is dispersed, is formed to be curved in one direction (azimuth direction), and further, grooves 2a for insertion of the one-dimensional arrays 1 are formed therein. The depth of the groove 2a is made slightly deeper than the insertion part of the substrate 10 (the length from the lower end of the substrate 10 to the lower end of the backing layer 15 shown in FIG. 2). This is for securing the space for providing the ground lead-out wire 28a and the address lead-out wires 28b of the one-dimensional array 1.

Figure 14:
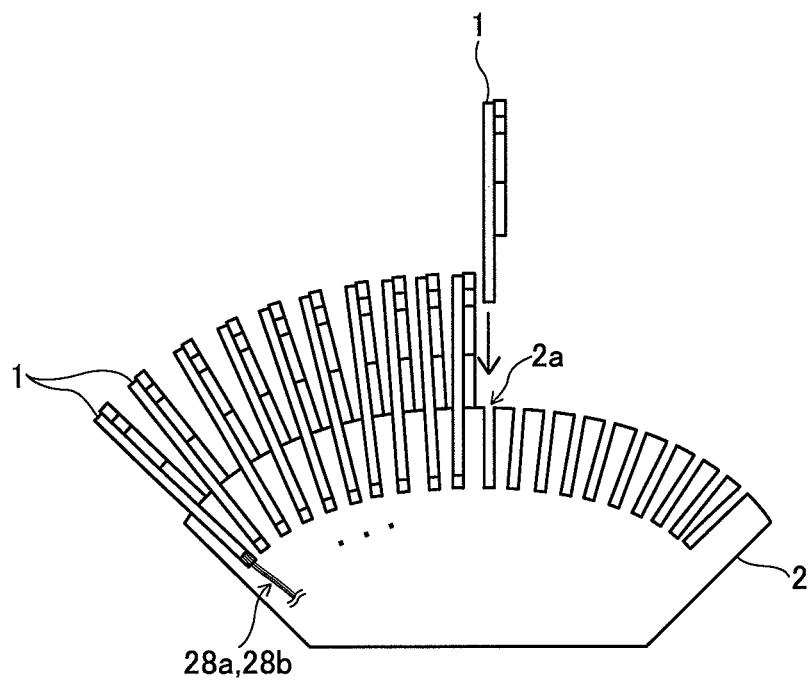
FIG. 14 is a diagram for explanation of the step of arranging one-dimensional arrays on the backing material.

Then, as shown in FIG. 14, the one-dimensional arrays 1 are inserted into the grooves 2a of the backing material 2. In this regard, it is desirable that the substrate 10 is fixed by providing adhesives in the grooves 2a. Furthermore, the ground lead-out wires 28a and the address lead-out wires 28b are led out from the bottom parts of the grooves 2a to the side of the backing material 2. Thereby, the ultrasonic probe shown in FIG. 1 is completed.

As explained above, according to the embodiment, the two-dimensional ultrasonic probe having the ultrasonic radiation surface of a desired shape can be manufactured easily.

In the embodiment, as shown in FIGS. 9 and 10, the ultrasonic transducer member 20 is bonded to the substrate 10, and then, the member is divided into the ultrasonic transducers 1a. However, plural ultrasonic transducers 1a that have been cut in a desired width may be arranged at desired intervals on the substrate 10.

Next, the second embodiment of the present invention will be explained.

The second embodiment is different from the first embodiment in that an integrated circuit is formed on the substrate 10 shown in FIG. 2, and the rest is the same as that in the first embodiment.

Figure 15:
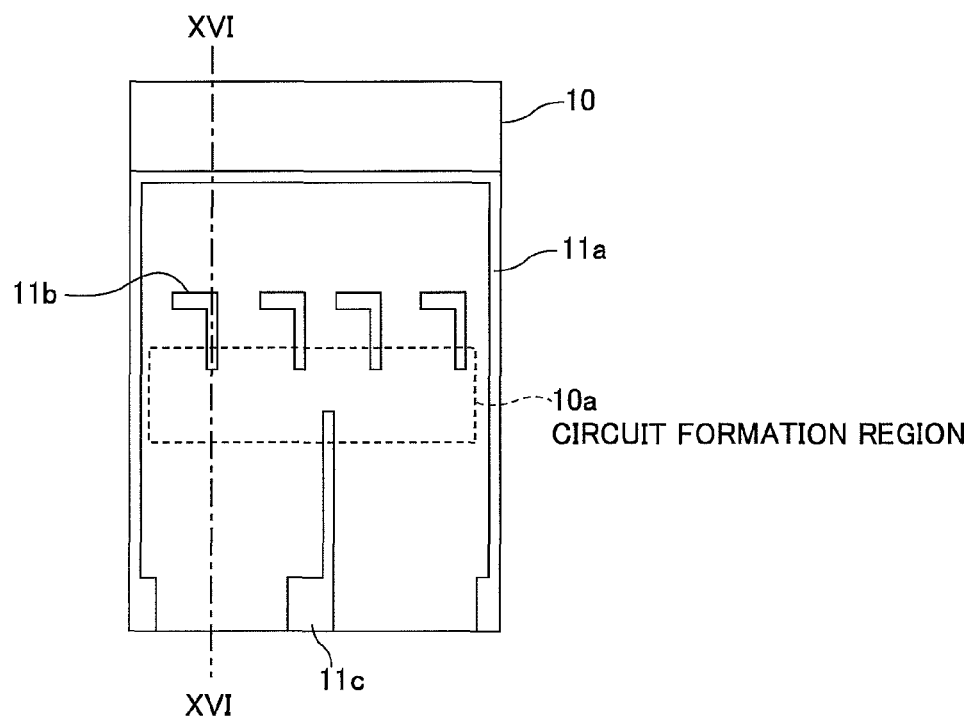
FIG. 15 is a plan view showing a substrate to be used in an ultrasonic probe according to the second embodiment of the present invention.

FIG. 15 is a plan view showing a substrate to be used in an ultrasonic probe according to the second embodiment of the present invention. In the embodiment, a semiconductor substrate of a silicon chip or the like is used as the substrate 10. An integrated circuit including plural MOSFETs (metal-oxide semiconductor field-effect transistors, hereinafter, simply referred to as "transistors") are formed in a circuit formation region 10a of the substrate 10. Further, a common wire 11a, individual wires 11b, and an input/output terminal 11c are formed on the substrate 10.

Figure 16:
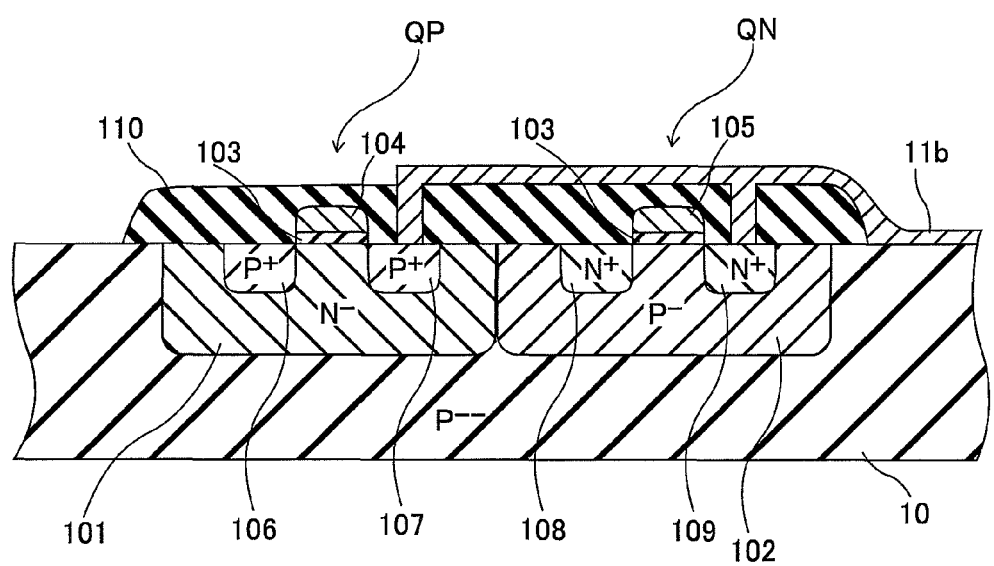
FIG. 16 is a sectional view showing a section of part of a circuit formation region along the dashed-dotted line XVI-XVI shown in FIG. 15.

FIG. 16 is a sectional view showing a section of part of the circuit formation region along the dashed-dotted line XVI-XVI shown in FIG. 15. As shown in FIG. 16, an N-well 101 and a P-well 102 are formed within the P-type substrate 10. On the other hand, gate electrodes 104 and 105 are formed with intervenient gate insulating films 103 on the substrate 10. P-type impurity diffusion regions 106 and 107 as a source and a drain are formed on both sides within the N-well 101, and thereby, a P-channel transistor QP is configured. Further, N-type impurity diffusion regions 108 and 109 as a source and a drain are formed on both sides within the P-well 102, and thereby, an N-channel transistor QN is configured. Furthermore, an interlayer insulating film 110 is formed on the substrate 10, and the individual wire 11b is connected to the source or drain of the transistors QP and QN via the through holes formed in the interlayer insulating film 110. Multilayer wiring may be realized by providing plural sets of interlayer insulating films and wiring layers.

Figure 17:
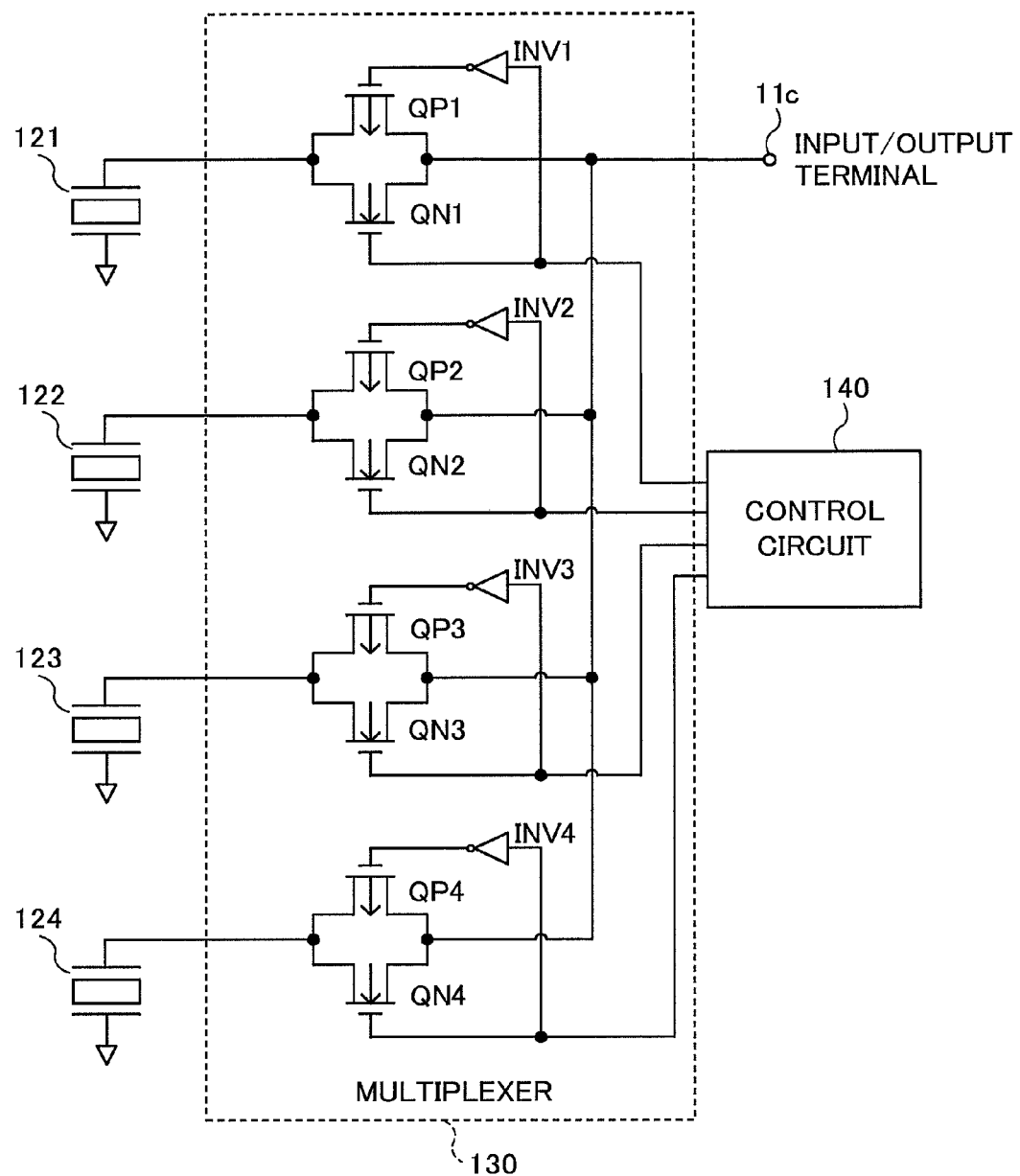
FIG. 17 is a circuit diagram showing a first circuit example formed in the circuit formation region shown in FIG. 15.

FIG. 17 is a circuit diagram showing a first circuit example formed in the circuit formation region shown in FIG. 15. In the first circuit example, a multiplexer 130 is connected to four vibrators 121-124, and thereby, one or some of these vibrators 121-124 are selectively connected to the input/output terminal 11c.

The multiplexer 130 includes a first analog switch configured of a P-channel transistor QP1 and an N-channel transistor QN1, a second analog switch configured of a P-channel transistor QP2 and an N-channel transistor QN2, a third analog switch configured of a P-channel transistor QP3 and an N-channel transistor QN3, a fourth analog switch configured of a P-channel transistor QP4 and an N-channel transistor QN4, and inverters INV1-INV4 that invert control signals supplied to the respective analog switches.

Further, in order to control the multiplexer 130, a control circuit 140 is provided. The control circuit 140 generates control signals for controlling the respective analog switches according to timing signals supplied via wireless or wired connection from outside the ultrasonic probe.

Figure 18:
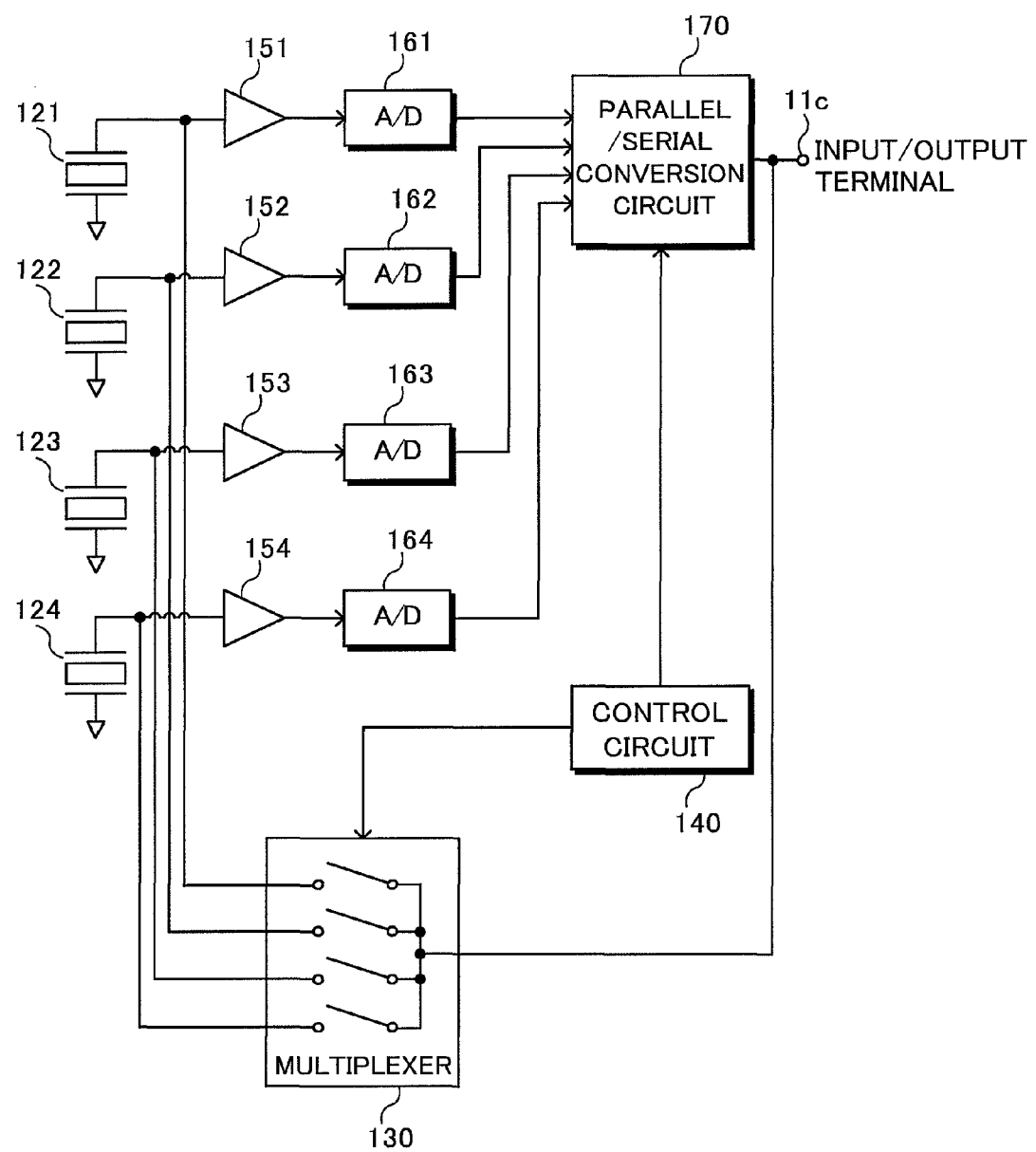
FIG. 18 is a circuit diagram showing a second circuit example formed in the circuit formation region shown in FIG. 15.

FIG. 18 is a circuit diagram showing a second circuit example formed in the circuit formation region shown in FIG. 15. In the second circuit example, preamplifiers 151-154 that amplify the electric signals outputted from the four vibrators 121-124 respectively, analog to digital converters (A/D converters) 161-164 that convert the output signals of the preamplifiers 151-154 into digital signals respectively, and a parallel/serial conversion circuit 170 that converts the parallel data outputted from the A/D converters 161-164 into serial data and supplies the serial data to the input/output terminal 11c are added to the first circuit example shown in FIG. 17. The parallel/serial conversion circuit 170 operates in synchronization with a clock signal generated by the parallel/serial conversion circuit 170 itself or a clock signal supplied via wireless or wired connection from outside the ultrasonic probe.

In the second circuit example, at the time of reception of ultrasonic waves, reception signals outputted from the four vibrators 121-124 are supplied as serial data to the input/output terminal 11c, and, at the time of transmission of ultrasonic waves, drive signals supplied to the input/output terminal 11c can be applied to one or some of the four vibrators 121-124.

According to the embodiment, microscopic wiring can be formed at low costs in a simple process. Thereby, the plural ultrasonic transducers 1a can be arranged with a narrow pitch. Therefore, an ultrasonic probe including a one-dimensional array or a two-dimensional array in which plural one-dimensional arrays are arranged can be downsized at low costs.

Further, according to the embodiment, the number of shield wires connected to the ultrasonic probe can be reduced. For example, when a two-dimensional array in which ultrasonic transducers are arranged in 32 rows×32 columns is formed, generally, 32×32=1024 shield wires are required. However, by providing a multiplexer to each one-dimensional array, the number of shield wires becomes 32. Accordingly, with 6-bit control wires, the number of wires may be suppressed to the total of 224 (32 shield wires and 6×32=192 control wires). As a result, the thickness of the cable for connection between the ultrasonic probe and the ultrasonic diagnostic apparatus main body can be reduced.

Figure 19:
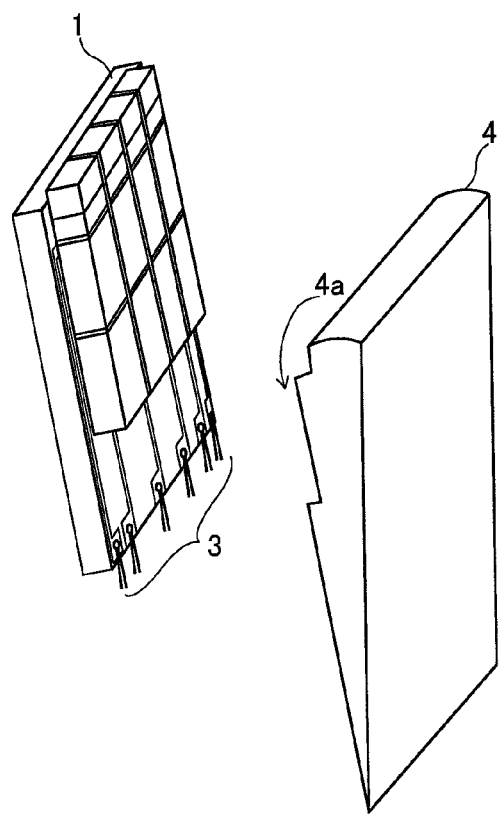
FIGS. 19-21 are diagrams for explanation of a method of manufacturing an ultrasonic probe according to the third embodiment of the invention.

Next, an ultrasonic probe according to the third embodiment of the invention and a method of manufacturing the probe will be explained with reference to FIGS. 19-21.

In the above explained first and second embodiments of the present invention, the two-dimensional array is formed by inserting plural one-dimensional arrays 1 (FIG. 1) into one backing material 2. However, this embodiment is characterized in that a backing material (also serves as a holding member) is joined to each one-dimensional array and plural backing materials are assembled for holding the two-dimensional array.

First, in the method of manufacturing the ultrasonic probe according to the first embodiment, a one-dimensional array 1 is fabricated in the same manner as that has been explained by referring to FIGS. 4-12, lead wires 3 (a ground lead-out wire 28a and address lead-out wires 28b shown in FIG. 11) are connected thereto. On the other hand, as shown in FIG. 19, a backing material 4 is fabricated by shaping a resin material or the like, in which ferrite powder or the like is dispersed, in a column having a sector bottom surface, and further, providing a notch in a part thereof.

Figure 20:
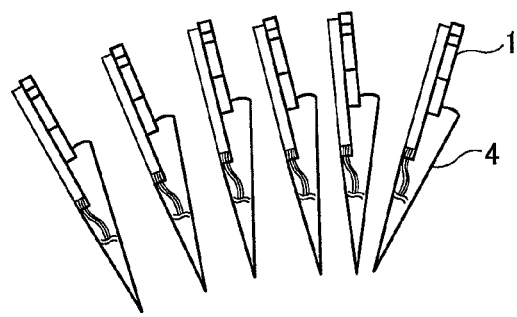

Then, as shown in FIG. 20, a part of the substrate 10 of the one-dimensional array 1 is bonded to the notch 4a of the backing material 4, and thereby, they are integrated. In this regard, the lead wires 3 are led out from the bottom of the notch 4a to the side. Thus integrated piece is fabricated in number corresponding to the number of one-dimensional arrays 1 to be arranged in the azimuth direction (FIG. 1).

Figure 21:
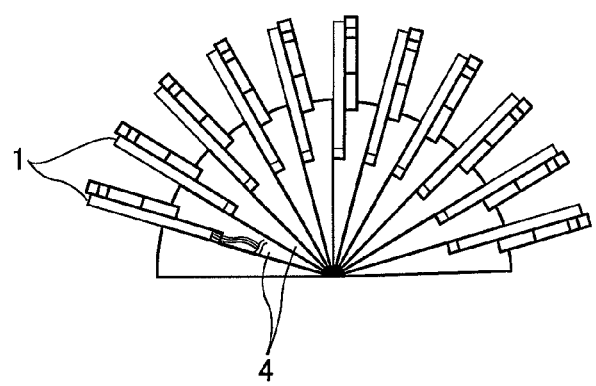

Furthermore, as shown in FIG. 21, plural pieces are assembled by joining the backing materials 4 to one another by using adhesives. Thereby, a two-dimensional ultrasonic probe having a curved ultrasonic radiation surface is completed.

Next, an ultrasonic probe according to the fourth embodiment of the invention will be explained with reference to FIGS. 22 and 23.

In the ultrasonic probes according to the first to third embodiments of the invention, a single-layer piezoelectric vibrator formed by forming electrode layers on both sides of one piezoelectric material is used, however, this embodiment is characterized in that a multilayered piezoelectric vibrator having plural piezoelectric material layers is used.

Figure 22:
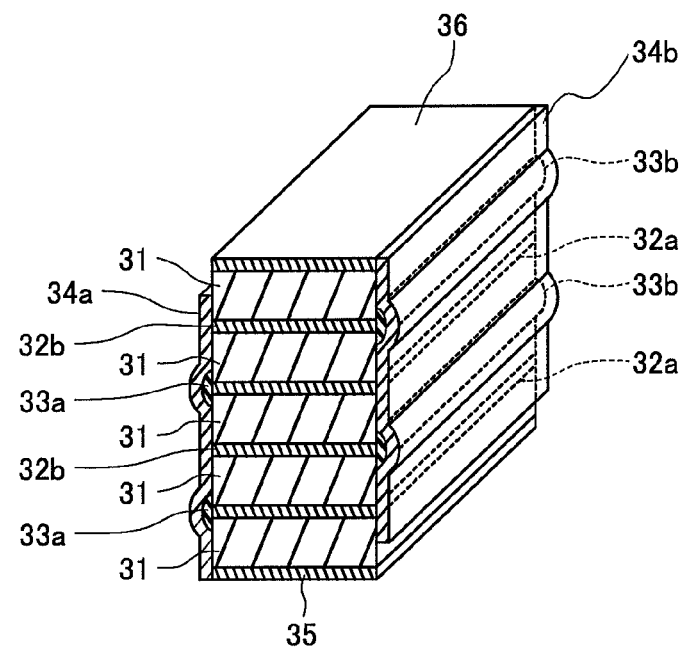
FIG. 22 is a partial sectional perspective view showing a multilayered piezoelectric vibrator to be used in an ultrasonic probe according to the fourth embodiment of the invention.

FIG. 22 is a partial sectional perspective view showing a structure of a multilayered piezoelectric vibrator. The multilayered piezoelectric vibrator 30 includes plural piezoelectric material layers 31, internal electrode layers 32a and 32b, insulating films 33a and 33b, side electrodes 34a and 34b, a lower electrode 35, and an upper electrode 36. The piezoelectric material layers 31 and the internal electrode layers 32a and 32b are alternately stacked.

The insulating film 33a is formed on one end (at the left of the drawing) of the internal electrode layer 32a, and thereby, the internal electrode layer 32a is insulated from the side electrode 34a and electrically connected to the side electrode 34b. Further, the insulating film 33b is formed on the other end (at the right of the drawing) of the internal electrode layer 32b, and thereby, the internal electrode layer 32b is insulated from the side electrode 34b and electrically connected to the side electrode 34a. Furthermore, the lower electrode 35 is connected to the side electrode 34a and the upper electrode 36 is connected to the side electrode 34b.

By providing the electrodes of the multilayered piezoelectric vibrator in this fashion, plural units, each including one piezoelectric material layer 31 and electrodes provided on both side thereof (e.g., internal electrode layers 32a and 32b) are connected in parallel. When a voltage is applied to the lower electrode 35 and the upper electrode 36 of the multilayered piezoelectric vibrator, opposite electric fields are alternatively applied to the plural piezoelectric material layers 31. Such a multilayered piezoelectric vibrator can substantially increase areas of opposed electrodes compared to the single-layered vibrator, and thus, can reduce the electric impedance. Therefore, the multilayered piezoelectric vibrator operates more efficiently for the applied voltage than the single-layered vibrator.

Figure 23:
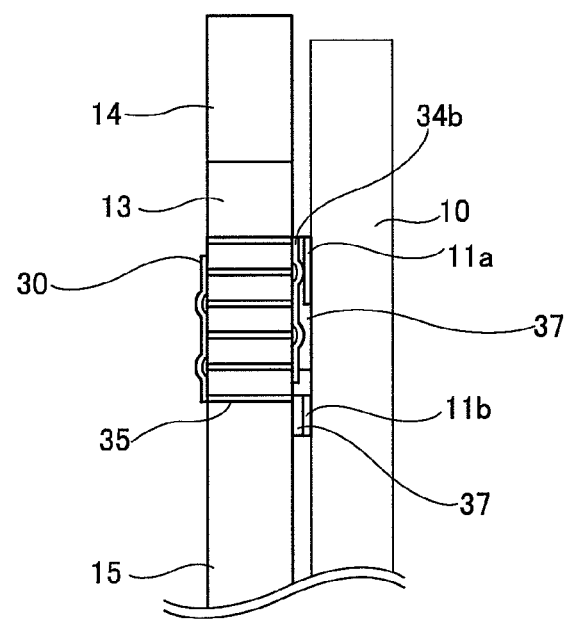
FIG. 23 is a schematic view showing a state in which the multilayered piezoelectric vibrator shown in FIG. 22 is joined to a substrate.

As shown in FIG. 23, when the multilayered piezoelectric vibrator 30 is attached to the substrate 10, electrically conductive pastes 37 may be used. Here, the side surface of the multilayered piezoelectric vibrator 30 partially rises due to the insulating films 33a and 33b, however, by providing the electrically conductive pastes 37 thicker, the side electrodes 34b (or 34a) and the lower electrode 35 (or the upper electrode 36) can be stably connected to the wires 11a and 11b of the substrate 10 despite the rise. Further, it is desirable to provide the electrically conductive pastes 37 thicker in order to reduce the braking on the expansion and contraction of the multilayered piezoelectric vibrator 30.

Next, an ultrasonic probe according to the fifth embodiment of the invention will be explained with reference to FIGS. 24 and 25.

Figure 24:
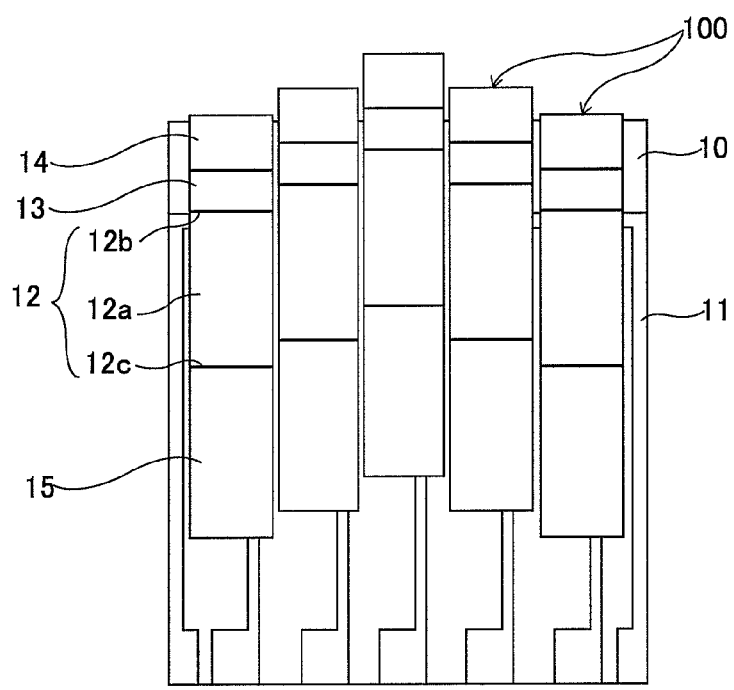
FIGS. 24 and 25 are diagrams for explanation of an ultrasonic probe according to the fifth embodiment of the invention.
Figure 25:
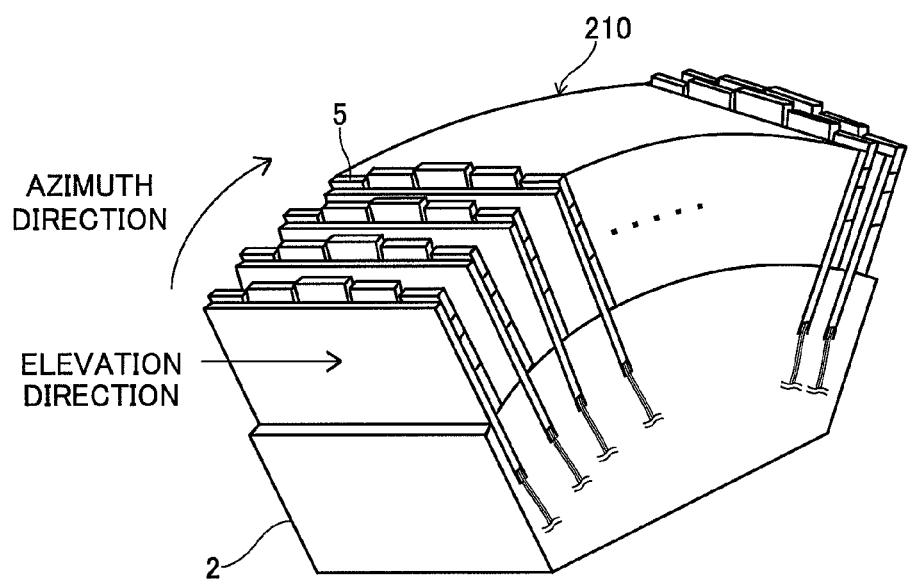

As shown in FIG. 24, in the embodiment, one ultrasonic transducer array 5 is fabricated by arranging plural ultrasonic transducers 1a on the substrate such that the heights of the respective ultrasonic radiation surfaces 100 differ from one another. Then, as shown in FIG. 25, the ultrasonic transducer arrays 5 are arranged in a backing material 2 having an upper surface formed to be curved in the azimuth direction. Thereby, an ultrasonic radiation surface 210 that curves not only in the azimuth direction but also in the elevation can be formed. By using a two-dimensional ultrasonic probe having the curved ultrasonic radiation surface 210, ultrasonic waves can be transmitted toward the wider region within the object.

Here, in FIG. 24, plural ultrasonic transducers 1a are arranged such that the plural ultrasonic radiation surfaces 100 are arranged in a convex shape, however, the plural ultrasonic radiation surfaces 100 maybe arranged in a concave shape. In this case, by driving the ultrasonic transducers 1a at the same time, an ultrasonic beam with a narrowed focus can be formed.

Figure 26:
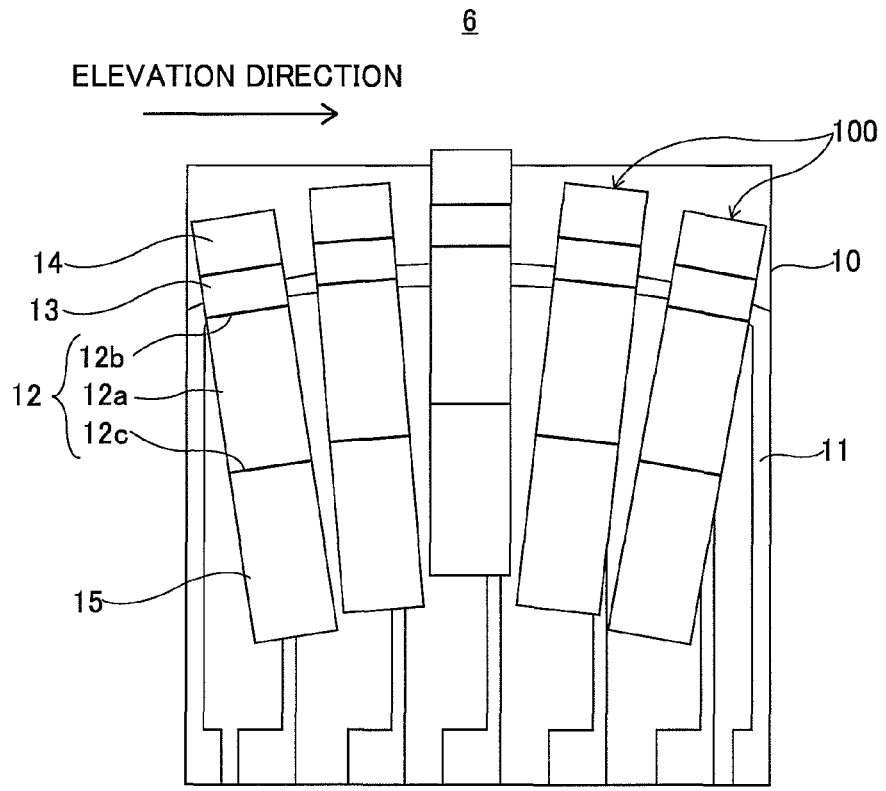
FIG. 26 is a diagram for explanation of an ultrasonic probe according to the sixth embodiment of the invention.

Next, an ultrasonic probe according to the sixth embodiment of the invention will be explained with reference to FIG. 26.

In the embodiment, the plural ultrasonic transducers 1a are radially arranged such that the respective ultrasonic radiation surfaces 100 are oriented in the different directions from one another. Then, the ultrasonic transducer arrays 6 are arranged in a backing material 2 (see FIG. 25) having an upper surface formed to be curved in the azimuth direction. Thereby, an ultrasonic radiation surface that curves not only in the azimuth direction but also in the elevation can be formed. In this case, the transmission region of ultrasonic waves in the elevation direction can be made wider than that shown in FIGS. 24 and 25.

Figure 27:
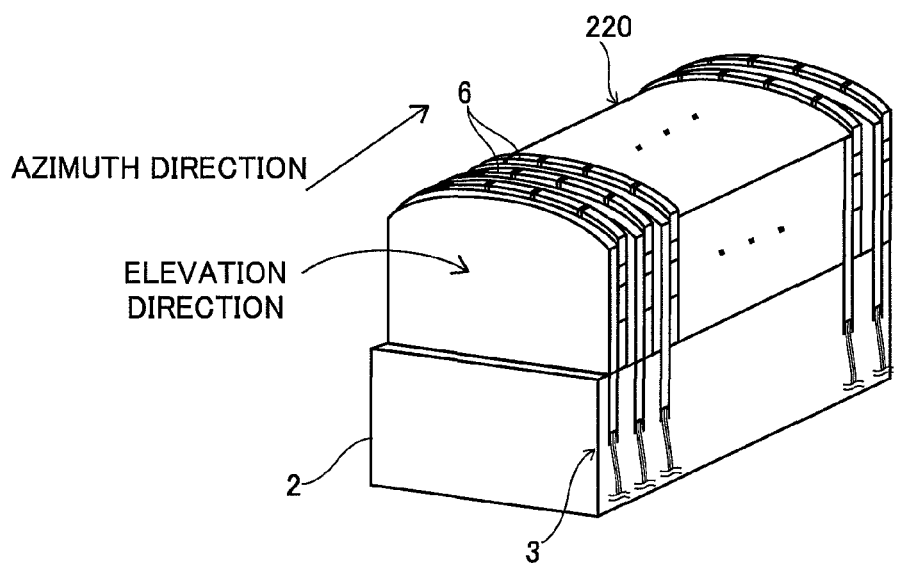
FIG. 27 is a perspective view showing a modified example of the ultrasonic probe according to the sixth embodiment of the invention.

Further, as a modified example of the ultrasonic probe according to the embodiment, a two-dimensional array may be formed by arranging plural ultrasonic transducer arrays 6 (FIG. 26) in parallel with one another as shown in FIG. 27. In this case, an ultrasonic radiation surface 220 that curves only in the elevation direction can be formed.

Next, modified examples of the ultrasonic probes according to the first to sixth embodiments of the present invention will be explained with reference to FIGS. 28 and 29.

In the above-explained ultrasonic probes according to the first to sixth embodiments, various kinds of ultrasonic transducer arrays can be fabricated by changing the shape of the backing material for holding the one-dimensional arrays 1 and the ultrasonic transducer arrays 5 and 6.

Figure 28:
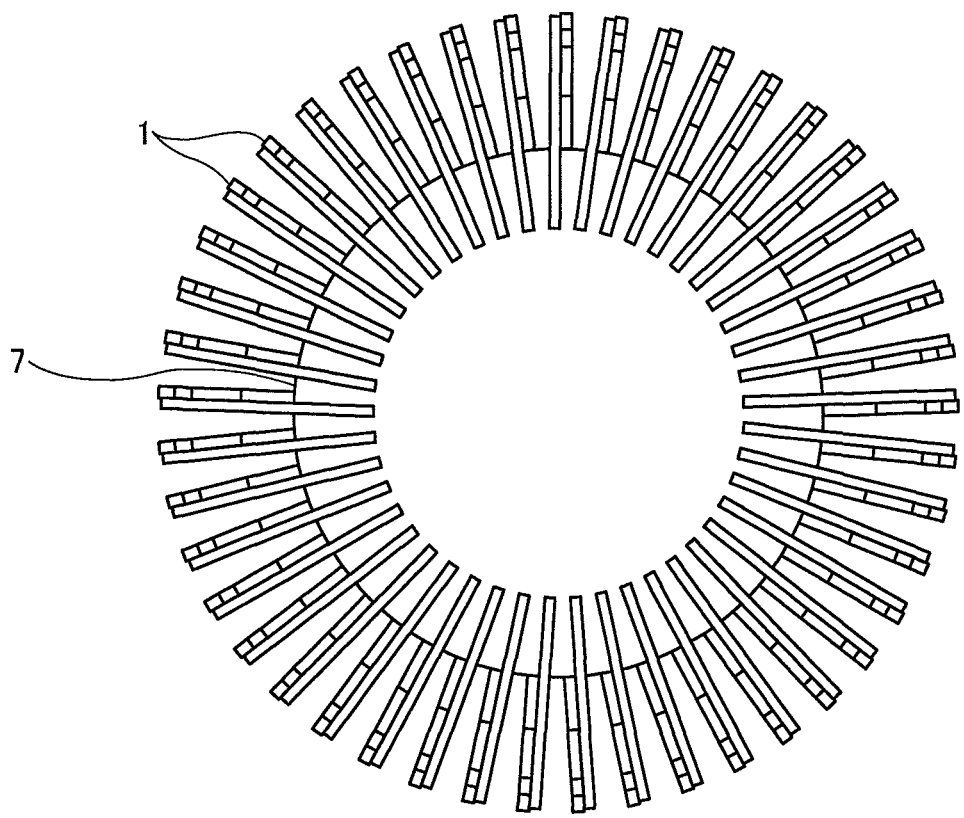
FIG. 28 shows a first modified example of the ultrasonic probes according to the first to sixth embodiments of the present invention.

As shown in FIG. 28, a radial ultrasonic transducer having a viewing angle of 360° can be fabricated by forming a cylindrical backing material 7 and arranging the one-dimensional arrays 1 to cover the entire side surface. The radial ultrasonic transducer is applied to an ultrasonic probe and an ultrasonic endoscope to be used for observation within the body cavity of the object. This modified example is effective because the downsizing of arrays and reduction in the cable thickness can be realized in the ultrasonic probe for intracavity scan or the like by combining the modified example with the ultrasonic probe according to the second embodiment including the multiplexers.

Figure 29:
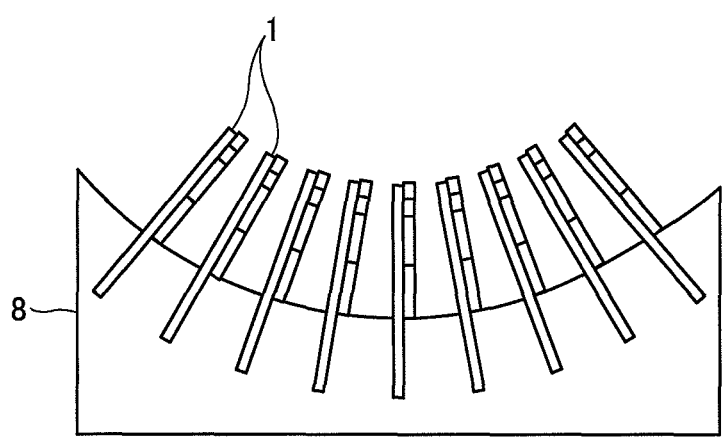
FIG. 29 shows a second modified example of the ultrasonic probes according to the first to sixth embodiments of the present invention.

Further, as shown in FIG. 29, a concave array that forms ultrasonic beams in transmission directions narrowed to some degree can be fabricated by shaping the upper surface of the backing material 8 to be a concave surface and arranging the one-dimensional arrays 1 on the upper surface.

The invention claimed is:

1. An ultrasonic probe comprising:
   plural ultrasonic transducer arrays, each including (i) a supporting material having a principal surface on which plural signal transmission paths are arranged, and (ii) plural ultrasonic transducers attached to the principal surface of said supporting material and one-dimensionally arranged in an elevation direction, each of said plural ultrasonic transducers having an ultrasonic radiation surface and a side surface on which two electrodes are arranged, and said side surface being attached to the principal surface of said supporting material such that said two electrodes are joined via electrically conductive pastes to selected two of the plural signal transmission paths arranged on the principal surface of said supporting material; and
   at least one holding member having a surface curved in an azimuth direction and formed with grooves each oriented in the elevation direction, the supporting materials of said plural ultrasonic transducer arrays being inserted into the grooves, and said at least one holding member being configured to hold said supporting materials such that said plural ultrasonic transducer arrays are radially arranged in the azimuth direction.

2. The ultrasonic probe according to claim 1, wherein the ultrasonic radiation surfaces of the ultrasonic transducers included in said plural ultrasonic transducer arrays are arranged along a curved surface.

3. The ultrasonic probe according to claim 1, wherein, on the principal surface of said supporting material, said plural ultrasonic transducers are arranged such that the ultrasonic radiation surfaces thereof are oriented in the same direction.

4. The ultrasonic probe according to claim 1, wherein, on the principal surface of said supporting material, said plural ultrasonic transducers are arranged such that the ultrasonic radiation surfaces thereof are oriented in different directions from one another.

5. The ultrasonic probe according to claim 1, wherein each of said plural ultrasonic transducers includes a multilayered piezoelectric vibrator having plural piezoelectric material layers and plural electrode layers configured to alternately apply opposite electric fields to said plural piezoelectric material layers.

6. The ultrasonic probe according to claim 1, wherein said supporting material includes at least one of silicon, silicon oxide, silicon carbide, glass epoxy, polyimide, alumina, and zirconia.

7. The ultrasonic probe according to claim 1, wherein said supporting material includes a silicon chip with an integrated circuit formed thereon.

8. The ultrasonic probe according to claim 7, wherein said supporting material includes a multiplexer configured to selectively connect said plural ultrasonic transducers to an input/output terminal.

9. The ultrasonic probe according to claim 8, wherein said supporting material further includes plural amplification circuits configured to amplify electric signals outputted from said plural ultrasonic transducers respectively, plural analog/digital converters (A/D converters) configured to convert output signals of said plural amplification circuits into digital signals respectively, and a parallel/serial conversion circuit configured to convert parallel digital signals outputted from said plural A/D converters into serial digital signals.

* * * * *